US005639631A

United States Patent [19]

Han et al.

[11] Patent Number: 5,639,631
[45] Date of Patent: Jun. 17, 1997

[54] STABLE REAGENT FOR FERRIC ION COMPLEX INDICATOR SYSTEMS

[75] Inventors: Chi-Neng Arthur Han, Philadelphia, Pa.; Kenneth J. Dean, Carmel, Ind.; Walter W. Jernigan; William R. Carr, both of Indianapolis, Ind.

[73] Assignee: Boehringer Mannheim Corporation, Indianapolis, Ind.

[21] Appl. No.: 493,727

[22] Filed: Jun. 22, 1995

Related U.S. Application Data

[63] Continuation of Ser. No. 952,445, Sep. 28, 1992, abandoned.

[51] Int. Cl.[6] ................ C12Q 1/28; C12Q 1/54; C12Q 1/00; C12N 9/04
[52] U.S. Cl. ................ 435/28; 435/14; 435/4; 435/190; 436/63; 436/74; 424/94.1
[58] Field of Search ................ 435/28, 14, 4, 435/190; 436/63, 74; 424/94.1

[56] References Cited

U.S. PATENT DOCUMENTS

| | | | |
|---|---|---|---|
| 4,576,913 | 3/1986 | Adachi et al. | 435/26 |
| 4,701,420 | 10/1987 | Thunberg et al. | 436/94 |
| 4,755,472 | 7/1988 | Ismail et al. | 436/66 |
| 4,929,545 | 5/1990 | Freitag | 435/28 |
| 4,942,127 | 7/1990 | Wada et al. | 435/14 |
| 5,334,508 | 8/1994 | Hoenes | 435/190 |
| 5,434,055 | 7/1995 | Jernigan | 435/4 |
| 5,508,171 | 4/1996 | Walling et al. | 435/14 |

FOREIGN PATENT DOCUMENTS

| | | | |
|---|---|---|---|
| 0 123 115 | 10/1984 | European Pat. Off. | C12Q 1/28 |
| 61-25498 | 2/1986 | Japan | C12Q 1/32 |

*Primary Examiner*—John Kight
*Assistant Examiner*—Louise Leary
*Attorney, Agent, or Firm*—D. Michael Young; Max J. Kenemore; Marilyn L. Amick

[57] ABSTRACT

The invention is a stable reagent used in assay systems that form a colored ferric ion complex, such as Prussian Blue. Such reagents are useful for the detection or measurement of an analyte from a fluid sample. Surprisingly, it has been found that the inclusion of certain ferric ion chelating agents, such as 3-sulfobenzoic acid, will inhibit formation of the blank reaction in the reagent.

20 Claims, No Drawings

STABLE REAGENT FOR FERRIC ION COMPLEX INDICATOR SYSTEMS

This is a continuation of application Ser. No. 07/952,445 filed on Sep. 28, 1992, now abandoned.

FIELD OF THE INVENTION

The invention relates to a stable reagent useful for forming a ferric ion chelation complex, as an indicator, in the detection or measurement of an analyte from a fluid sample. The invention also relates to a method of making a stable reagent, incorporating the reagent into an analytical element, and a method of determining the presence of an analyte in a liquid sample.

BACKGROUND OF THE INVENTION

Many clinical chemistry assays are performed using reagents that form colored indicators. In such assays, the intensity of the color of the indicator is correlated to the concentration of analyte in the fluid sample being measured.

Exemplary of such assays is the analysis of glucose from a blood sample by utilizing a reagent that forms Prussian Blue (or Turnbull's Blue) as a colored indicator. The reagent may include the enzyme glucose oxidase (GOD), and potassium ferricyanide and ferric sulfate for the formation of Prussian Blue. The reaction that generates Prussian Blue may be depicted as follows (Scheme I):

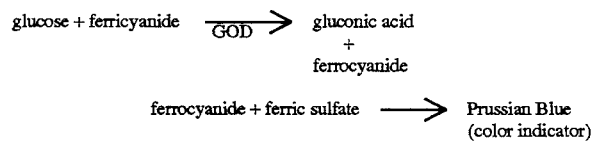

Accordingly, the more Prussian Blue that is formed by this reaction, then the more glucose is present in the blood sample being analyzed.

However, a particular problem with reagents that are used to form the Prussian Blue indicator, and other reagents that are used to form indicators that involve ferric ion complexes, is stability. Such reagents, when in liquid form, are unstable to light and heat, and, when in lyophilized form or included in a film, are additionally unstable to humidity. In the case of a reagent useful for forming the Prussian Blue indicator in a glucose assay, the instability is manifested by premature formation of Prussian Blue ("the blank reaction") in the reagent prior to addition of a blood sample containing glucose.

SUMMARY OF THE INVENTION

The invention is a stable reagent used in assay systems that form a colored ferric ion complex, such as Prussian Blue. Such reagents are useful for the detection or measurement of an analyte from a fluid sample. However, in liquid form these reagents are unstable to heat and light. In lyophilized form or in a film, these reagents are further unstable to humidity. This instability is often manifested in the form of a blank reaction. For example, in a reagent used for forming the colored complex Prussian Blue, Prussian Blue is prematurely formed in the reagent.

Surprisingly, it has been found that the inclusion of certain ferric ion chelating agents, such as 3-sulfobenzoic acid, will inhibit formation of the blank reaction in the reagent.

DESCRIPTION OF THE INVENTION

The present invention is a stable reagent, capable of forming a ferric ion colored complex in the presence of an analyte from a fluid sample, and useful for the detection or measurement of the analyte from the fluid sample. At a minimum, the reagent includes a first compound that will react in a reaction involving the analyte to form a second compound that complexes with ferric ion to form a colored complex;

a source of ferric ions;

and a ferric ion chelator of sufficient type and in sufficient amount to substantially inhibit formation of the colored complex prior to addition of the analyte to the reagent and to substantially not inhibit formation of the colored complex after addition of the analyte to the reagent. Ferric ion chelators, such as citric acid, aspartic acid, ethylenediamine tetraacetic acid (EDTA), and succinic acid, which have too high an affinity for ferric ion are not of the type of ferric ion chelators included in this invention.

When the colored complex is Prussian Blue, the first compound may be a ferricyanide, such as potassium ferricyanide, the second compound may be a ferrocyanide, the source of ferric ions may be ferric sulfate, and the ferric ion chelator may be 3-sulfobenzoic acid, 3-hydroxybutyric acid, 4-hydroxybutyric acid, 5-aminovaleric acid, butyric acid, or propionic acid, or salts thereof. (see Scheme I in Background of the Invention section.) The ferric ion chelator may also be 2-sulfobenzoic acid, or tartaric acid, or a salt thereof.

Importantly, inclusion of the ferric ion chelator, of the type specified herein, stabilizes a liquid reagent against heat and light and stabilizes a dry reagent (lyophilized or in a film) against heat, light and humidity. A molar ratio of about 3:1 ferric ion chelator:ferric ion in the reagent is sufficient to stabilize the reagent. The reagent will be increasingly stabilized with molar ratios of ferric ion chelator to ferric ion above about 3:1. The increased stabilization will be beneficial until the ratio of ferric ion chelator to ferric ion becomes high enough to deleteriously affect the reaction kinetics of the assay, that is, the colored complex (e.g., Prussian Blue) forms too slowly in the assay, and, as a result, assay time becomes too long and precision and accuracy of measurement are adversely affected.

A catalyst is preferably included in the reagent. The catalyst should be of sufficient type and in sufficient amount to catalyze the reaction involving the analyte and the first compound. When the analyte is glucose, the catalyst may be the enzyme glucose oxidase.

A buffer is also preferably included, and when 2-sulfobenzoic acid is used a buffer should be included, in the reagent. The buffer should be of sufficient type and in sufficient amount to provide a desired pH for the reagent and the reaction involving the analyte and the first compound. Further, the buffer should not deleteriously bind to ferric ion. For example, phosphate buffer precipitates ferric ion and should not be used in the reagent. In diagnostic assays, biological buffers, such as "Good" buffers (available from, e.g., Sigma Chemical Company) are often used buffers. Pyruvic acid, 2-amino butyric acid, gluconic acid, and 2-hydroxyisobutyric acid are useful buffers. The particular buffer used will depend upon the particular assay system being employed. For a reagent that is capable of forming the Prussian Blue indicator in a diagnostic assay, 4-amino butyric acid is a useful buffer.

The buffer may even be a weak chelator of ferric ion as long as the buffer does not substantially inhibit formation of the colored complex (the indicator) after the addition of the analyte to the reagent. If the buffer does weakly chelate ferric ion, then a lesser amount of ferric ion chelator (that is, less than a 3:1 molar ratio of ferric ion chelator to ferric ion) may be needed to stabilize the reagent.

The reagent may be formulated in liquid (aqueous) form, in lyophilized form, or incorporated into a film or a diagnostic kit. When incorporated into a film, a film former, for example, an aqueous vinyl propionate/vinyl acetate copolymer dispersion sold under the mark PROPIOFAN® 70 D (obtained from BASF) or a polyvinylacetate ethylene copolymer, such as film formers sold under the mark ELVACE (available from Reichhold Chemicals) or AIRFLEX 300 (available from Air Products), is needed. Other additives may be helpful in producing a film that incorporates the reagent of the present invention. For example, a viscosity controlling agent, such as hydroxy-methyl cellulose, a surfactant, such as polyoxyethylene-sorbitan monolaurate, an anti-foaming agent, such as acetone, and a film opener, such as diatomaceous earth or the film openers disclosed in Vogel et al., U.S. Pat. No. 4,312,834, issued Jan. 26, 1982, the disclosure of which is hereby incorporated by reference, may be helpful additives in formulating a film. Addition of a pigment, such as titanium dioxide, may be helpful in reflectance films; and addition of an oxidizing agent, such as potassium dichromate, may further increase the stability of a film that includes the reagent of the present invention by providing an oxidizing environment.

The present invention is generally applicable to any reagent that includes a source of ferric ions and that forms, as an indicator, a colored ferric ion chelation complex in the detection or measurement of an analyte from a fluid sample. Including a ferric ion chelator that substantially inhibits formation of the colored ferric ion chelation complex prior to addition of the analyte to the reagent and that does not substantially inhibit formation of the colored ferric ion chelation complex after addition of the analyte to the reagent will protect the reagent from the destabilizing effects of heat and light, if the reagent is in liquid form, and additionally from humidity, if the reagent is in dry form (lyophilized or incorporated in a film).

The present invention is specifically applicable to the compositions, methods, and analytical elements described in Freitag, U.S. Pat. No. 4,929,545, issued May 29, 1990, the disclosure of which is hereby incorporated by reference. In any of the examples found in the U.S. Pat. No. 4,929,545, a reagent that is stable to heat and light, if the reagent is in liquid form, and additionally stable to humidity, if the reagent is incorporated into a film on a test strip, may be prepared by adding to the reagent an amount of ferric ion chelator sufficient to make the molar ratio of ferric ion chelator to ferric ion about 3:1. Increasing this molar ratio will further stabilize the reagent until the ratio becomes high enough to deleteriously affect the reaction kinetics of an analyte assay that utilizes the reagent. The molar ratio of ferric ion chelator to ferric ion may become so high that assay time is too long and assay accuracy and precision become poor.

Another example of a reagent, or coating mass as it is referred to in Example 3 of U.S. Pat. No. 4,929,545, is as follows:

Step No. 1

Thoroughly mix 1376 grams(g) water, 58 g sodium hydroxide (pellets), 52 g 4-amino butyric acid, 331 g 3-sulfobenzoic acid, 52 g ferric sulfate, and 234 g potassium ferricyanide, thereby forming a penultimate aqueous ionic mixture. The penultimate aqueous ionic mixture is filtered to remove large particles and impurities. 0.17 g potassium dichromate, 288 g diatomaceous earth (available from Eagle-Picher Minerals, Inc. under the mark CELABRITE), and a sonicated suspension of 414 g titanium dioxide in 907 g water are mixed into the resulting filtrate, thereby forming the ultimate aqueous ionic mixture.

Step No. 2

Thoroughly mix 1067 g water, 1739 g PROPIOFAN® 70 D film former that has been demonomerized, 485 g of 4% aqueous hydroxymethyl cellulose (sold under the mark NATROSOL), 75 g acetone, and 4.7 g polyoxyethylenesorbitan monolaurate surfactant (sold under the mark TWEEN 20), thereby forming a polymer mixture. This mixture is filtered to remove large particles and impurities.

Step No. 3

Thoroughly mix 368 g water and 64 g glucose oxidase (G02A grade having 185 kilounits glucose oxidase/g, available from Biozyme Laboratories International, Ltd.), thereby forming an enzyme mixture. This enzyme mixture is filtered.

Step No. 4

With mixing, the ultimate aqueous ionic mixture is slowly added to the filtrate of the polymer mixture. Once addition is complete, the filtrate of the enzyme mixture is added to form the penultimate coating mass, which is filtered to form the ultimate coating mass.

The ultimate coating mass may be coated onto a clear, polyester foil, as described in U.S. Pat. No. 4,929,545, Example 3 (col. 6), and dried to form a film coated test strip. This test strip may be used in detecting or measuring glucose in a fluid sample as described in Example 3 (col. 6) of U.S. Pat. No. 4,929,545.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

We claim:

1. A reagent useful for the detection or measurement of an analyte from a fluid sample, comprising:
   (a) a first compound that will react in a reaction involving the analyte to form a second compound that complexes with ferric ion to form a colored complex;
   (b) a source of ferric ions; and
   (c) a ferric ion chelator selected from the group consisting of 3-sulfobenzoic acid, 2-sulfobenzoic acid, tartaric acid, 3-hydroxybutyric acid, 4-hydroxybutyric acid, 5-aminovaleric acid, butyric acid, propionic acid, and salts thereof in sufficient amount to inhibit a blank reaction in the reagent.

2. The reagent of claim 1, further comprising:
   (d) a catalyst of sufficient type and in sufficient amount to catalyze the reaction involving the analyte and first compound.

3. The reagent of claim 1, wherein the molar ratio of ferric ion chelator to ferric ion is at least about 3:1.

4. The reagent of claim 2, further comprising:
   (e) a buffer of sufficient type and in sufficient amount to provide a desired pH for the reagent and the reaction involving the analyte and first compound and which will not deleteriously bind ferric ion.

5. The reagent of claim 4, wherein the catalyst is an enzyme.

6. The reagent of claim 5, wherein the molar ratio of ferric ion chelator to ferric ion is at least about 3:1.

7. The reagent of claim 5, wherein the reagent is an aqueous reagent.

8. The reagent of claim 5, further comprising:
(f) at least one film-forming agent in sufficient amount to form a film.

9. The reagent of claim 7, wherein the first compound is ferricyanide, the second compound is ferrocyanide, and the colored complex is Prussian Blue.

10. The reagent of claim 7, wherein the first compound is ferricyanide, the second compound is ferrocyanide, the colored complex is Prussian Blue, and the ferric ion chelator is 3-sulfobenzoic acid or a salt thereof.

11. The reagent of claim 8, wherein the first compound is ferricyanide, the second compound is ferrocyanide, the colored complex is Prussian Blue, and the ferric ion chelator is 3-sulfobenzoic acid, 2-sulfobenzoic acid, tartaric acid, 3-hydroxybutyric acid, or 4-hydroxybutyric acid, or a salt thereof.

12. The reagent of claim 8, wherein the first compound is ferricyanide, the second compound is ferrocyanide, the colored complex is Prussian Blue, and the ferric ion chelator is 3-sulfobenzoic acid or a salt thereof.

13. The reagent of claim 9, wherein the molar ratio of ferric ion chelator to ferric ion is at least about 3:1.

14. The reagent of claim 11, wherein the molar ratio of ferric ion chelator to ferric ion is at least about 3:1.

15. A method of stabilizing a reagent that includes a source of ferric ions and a first compound that will react in a reaction involving an analyte from a fluid sample to form a second compound that complexes with ferric ion to form a colored complex, comprising:

adding to the reagent 3-sulfobenzoic acid, 2-sulfobenzoic acid, tartaric acid, 3-hydroxybutyric acid, 4-hydroxybutyric acid, 5-aminovaleric acid, butyric acid, or propionic acid, or a salt thereof in sufficient amount to inhibit a blank reaction in the reagent.

16. A method of stabilizing a reagent that includes a source of ferric ions and ferricyanide, which will react in a reaction involving an analyte from a fluid sample to form ferrocyanide, which complexes to ferric ion to form Prussian Blue, comprising:

adding 3-sulfobenzoic acid, 2-sulfobenzoic acid, tartaric acid, 3-hyroxybutyric acid, 4-hydroxybutyric acid, 5-aminovaleric acid, butyric acid, or propionic acid, or a salt thereof in sufficient amount to inhibit a blank reaction in the reagent.

17. A composition used specifically for the detection or measurement of an analyte in a fluid sample, comprising:

(a) an enzyme which specifically reacts with said analyte;
(b) a soluble ferricyanide compound which is reducible in the presence of an electron to produce a ferrocyanide compound;
(c) a soluble ferric compound which reacts with a ferrocyanide compound to form a reaction product therebetween;
(d) a buffer which does not prevent formation of said reaction product; and
(e) 3-sulfobenzoic acid, 2-sulfobenzoic acid, tartaric acid, 3-hydroxybutyric acid, 4-hydroxybutyric acid, 5-aminovaleric acid, butyric acid, or propionic acid, or a salt thereof in sufficient amount to inhibit a blank reaction in the composition, wherein the composition has a pH from about 3.0 to about 6.0.

18. The composition of claim 17 in lyophilized form.

19. A method for determining the presence of an analyte in a liquid sample, comprising:

contacting the liquid sample with the composition of claim 17, wherein formation of said reaction product is indicative of the presence of said analyte in said sample.

20. An analytical element useful in determining an analyte in a sample, comprising:

(a) a support carrier; and
(b) a reagent layer applied to said support carrier, said reagent layer comprising
  (i) an inert film,
  (ii) an enzyme which specifically reacts with said analyte,
  (iii) a soluble ferricyanide compound which is reduced in the presence of an electron to a ferrocyanide compound,
  (iv) a soluble ferric compound which reacts with said ferrocyanide compound to form a reaction product,
  (v) a buffer which does not prevent formation of said reaction product, and
  (vi) 3-sulfobenzoic acid, 2-sulfobenzoic acid, tartaric acid, 3-hydroxybutyric acid, 4-hydroxybutyric acid, 5-aminovaleric acid, butyric acid, or propionic acid, or a salt thereof in sufficient amount to inhibit a blank reaction in said reagent layer, wherein said reagent layer has a pH from about 3.0 to about 6.0.

* * * * *